United States Patent
Noshi et al.

(10) Patent No.: US 7,693,252 B2
(45) Date of Patent: Apr. 6, 2010

(54) MEDICAL IMAGE DISPLAY APPARATUS AND MEDICAL IMAGE DISPLAY SYSTEM

(75) Inventors: Yasuhiro Noshi, Nasushiobara (JP); Satoru Nakanishi, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/447,117

(22) Filed: Jun. 6, 2006

(65) Prior Publication Data
US 2006/0274877 A1 Dec. 7, 2006

(30) Foreign Application Priority Data
Jun. 6, 2005 (JP) ............... 2005-165726

(51) Int. Cl.
*A61B 6/00* (2006.01)
(52) U.S. Cl. .......................................... 378/4
(58) Field of Classification Search ............... 378/4–21, 378/901
See application file for complete search history.

(56) References Cited

U.S. PATENT DOCUMENTS

| | | | | |
|---|---|---|---|---|
| 4,135,247 A * | 1/1979 | Gordon et al. | ................. | 378/11 |
| 4,729,100 A * | 3/1988 | Tsujii | ............................ | 378/4 |
| 5,115,394 A * | 5/1992 | Walters | ...................... | 382/131 |
| 5,379,333 A * | 1/1995 | Toth | ............................. | 378/16 |
| 5,533,091 A * | 7/1996 | Hsieh | .......................... | 378/210 |
| 5,583,903 A * | 12/1996 | Saito et al. | ..................... | 378/19 |
| 5,615,279 A * | 3/1997 | Yoshioka et al. | ............ | 382/131 |
| 6,094,469 A * | 7/2000 | Dobbs et al. | ................... | 378/19 |
| 6,215,842 B1 * | 4/2001 | Resnick et al. | ................ | 378/16 |
| 6,493,416 B1 * | 12/2002 | Hsieh | ........................... | 378/4 |
| 6,542,576 B2 * | 4/2003 | Mattson | ...................... | 378/119 |
| 6,744,846 B2 * | 6/2004 | Popescu et al. | ............... | 378/16 |
| 6,793,496 B2 * | 9/2004 | Edic et al. | .................... | 434/262 |
| 7,039,163 B2 * | 5/2006 | Popescu et al. | ............. | 378/109 |
| 7,187,794 B2 * | 3/2007 | Liang et al. | ................. | 382/131 |
| 2004/0017880 A1 * | 1/2004 | Toth et al. | ...................... | 378/4 |
| 2004/0032928 A1 * | 2/2004 | Toth et al. | ................... | 378/108 |
| 2004/0062341 A1 | 4/2004 | Popescu et al. | ................ | 378/4 |
| 2005/0008115 A1 | 1/2005 | Tsukagoshi | .................... | 378/4 |

* cited by examiner

*Primary Examiner*—Edward J Glick
*Assistant Examiner*—Alexander H Taningco
(74) *Attorney, Agent, or Firm*—Oblon, Spivak, McClelland, Maier & Neustadt, L.L.P.

(57) ABSTRACT

Noise originating from the difference between a second dose as an X-ray dose used for simulation and a first dose as an X-ray dose associated with raw data obtained by past imaging operation is calculated. Simulation pure raw data as information associated with a photon count and noise which are predicted to be detected by a plurality of X-ray detection elements when imaging is performed by using X-rays of the second dose is generated on the basis of the calculated noise and the raw data obtained by past imaging operation. A simulation image predicted to be obtained by imaging operation using X-rays of the second dose is generated by using the simulation pure raw data and displayed.

9 Claims, 8 Drawing Sheets

MEDICAL IMAGE DISPLAY APPARATUS AND MEDICAL IMAGE DISPLAY SYSTEM

CROSS-REFERENCE TO RELATED APPLICATIONS

This application is based upon and claims the benefit of priority from prior Japanese Patent Application No. 2005-165726, filed Jun. 6, 2005, the entire contents of which are incorporated herein by reference.

BACKGROUND OF THE INVENTION

1. Field of the Invention

The present invention relates to a medical image display apparatus and medical image display system which execute noise addition simulation used before X-ray computed tomography.

2. Description of the Related Art

As is well known, an X-ray computed tomography apparatus is designed to obtain an image (tomogram) by calculating (reconstructing) the X-ray absorptance of a tissue such as an organ on the basis of the amount of X-rays absorbed in a subject to be examined as an index called a CT value with reference to the X-ray absorptance of water.

A reconstructed image inevitably contains image noise. Image noise is typically defined with reference to a variation in the CT value of a homogeneous phantom image as a standard deviation, which is generally called an image SD. In order to make diagnosis by observing a reconstructed image, e.g., to discriminate a shadow on the image as noise or a tumor, the image SD unique to the image must be considered.

In performing this X-ray computed tomography, a simulation image is sometimes generated by, for example, adding noise to an image obtained by past imaging operation to support decision of scan conditions under which a smaller dose of X-rays is allowed. An apparatus which realizes such support is called a scan plan simulator, with which a simulation image can be generated before CT scanning by inputting a region to be scanned, a body thickness, and scan conditions.

Note that a scan condition indicates at least one of the following: "scan mode", "ON/OFF of an exposure reducing function", "imaging slice thickness", "image slice thickness", "FOV", "helical pitch", "reconstruction function", "tube voltage", "tube current", and "scan speed".

The conventional scan plan simulator, however, has the following problems.

When simulation images are to be generated on a CT image basis, noise due to image reconstruction cannot be added. In addition, when simulation images are to be generated on a CT image basis, for example, artifacts originating from bones cannot be precisely reproduced theoretically. Therefore, for example, an unnecessarily good image SD (i.e., an unnecessarily high X-ray intensity) of an image obtained by actual imaging is obtained for an obtained simulation image. In contrast, a desired image SD cannot be obtained, and re-scanning is required. Either may lead to excessive X-ray exposure.

BRIEF SUMMARY OF THE INVENTION

The present invention has been made in consideration of the above situation, and has as its object to provide a medical image display apparatus and medical image display system which can generate a simulation image similar to an image obtained by actual imaging operation as compared with the prior art.

According to an aspect of the present invention, there is provided a medical image display apparatus which generates a computed tomogram, which is to be obtained by X-ray computed tomography, by simulation in a simulated manner, comprising: a storage unit which stores first projection data obtained on the basis of exposure of X-rays to a subject to be examined; an input unit to input information with respect to X-ray dose; a calculation unit which calculates noise information on the basis of the information with respect to X-ray dose; a projection data generating unit which generates second projection data on the basis of the first projection data and the noise information, the second projection data being predicted to be obtained by X-ray computed tomography using the information with respect to X-ray dose; and an image generating unit which generates a simulation image by using the second projection data.

According to another aspect of the present invention, there is provided a system for displaying of a diagnostic image on a computer system enabling the computer system, comprising: a computer code device configured to input information with respect to X-ray dose; a computer code device configured to calculate noise information on the basis of the information with respect to X-ray dose; a computer code device configured to generate second projection data, which is predicted to be obtained by X-ray computed tomography using the information with respect to X-ray dose, on the basis of first projection data obtained on the basis of exposure of X-rays to a subject and the noise information; and a computer code device configured to generate a simulation image by using the second projection data.

According to yet another aspect of the present invention, there is provided an X-ray computed tomography apparatus comprising: a storage unit which stores first projection data obtained on the basis of exposure of X-rays to a subject to be examined; an input unit to input information with respect to X-ray dose used for the simulation; a calculation unit which calculates noise information on the basis of the information with respect to X-ray dose; a projection data generating unit which generates second projection data, which is predicted to be obtained by X-ray computed tomography using the information with respect to X-ray dose, on the basis of the first projection data and the noise information; and an image generating unit which generates a simulation image by using the second projection data.

DETAILED DESCRIPTION OF THE INVENTION

An embodiment of the present invention will be described with reference to the views of the accompanying drawing. Note that the same reference numerals in the following description denote constituent elements having substantially the same functions and arrangements, and a repetitive description thereof will be made only when required. The following embodiment will exemplify a noise addition simulator as a discrete unit connected to, for example, a medical image device through a network. However, the present invention is not limited to this, and may be implemented by a program or the like which causes an X-ray computed tomography apparatus, viewer, personal computer, or medical workstation which incorporates the noise addition simulator to execute noise addition simulation. When the present invention is implemented by the program, in particular, the program can be distributed by being stored in recording media such as magnetic disks (floppy (registered trademark) disks, hard disks, and the like), optical disks (CD-ROMs, DVDs, and the like), and semiconductor memories.

Figure 1:
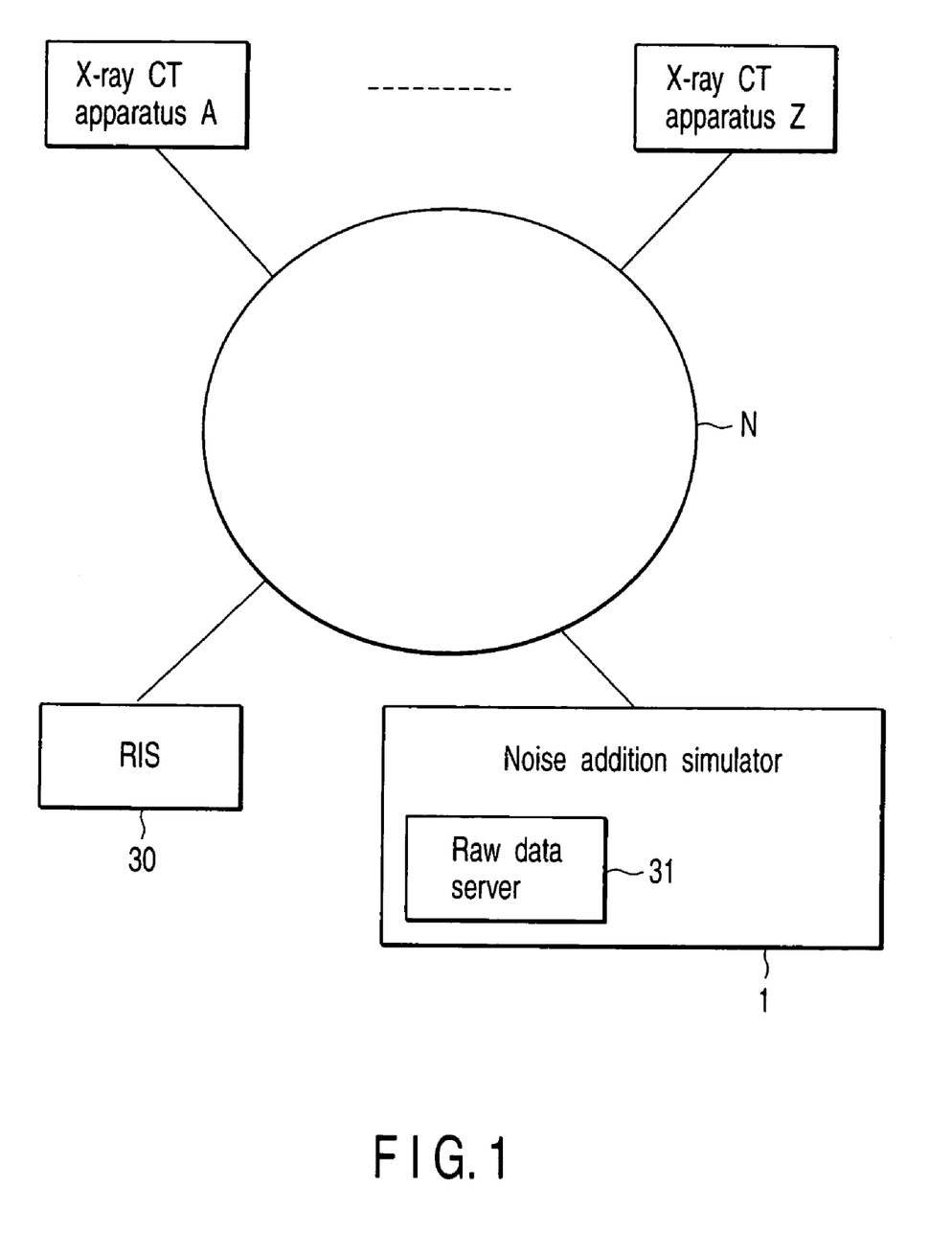
FIG. 1 is a view showing an example of a network arrangement including a noise addition simulator 1 according to this embodiment.

FIG. 1 shows an example of a network arrangement including a noise addition simulator 1 according to this embodiment. As shown in FIG. 1, the noise addition simulator 1 is connected to X-ray CT apparatuses A to Z and an RIS (Radiology Information System) server 30 through a network N, and can freely transmit/receive patient information, image data, and the like.

The noise addition simulator 1 comprises a raw data server 31. In this case, the raw data server 31 is a database dedicated to raw data which is constructed on an operating system such as Windows (registered trademark). The raw data server 31 is configured to transmit/receive data to/from at least one of the X-ray CT apparatuses A to Z through the network N and store the data. By allowing the raw data noise addition simulator to operate in cooperation with the raw data server in this manner makes it possible to select optimal raw data from a large amount of raw data.

Figure 2:
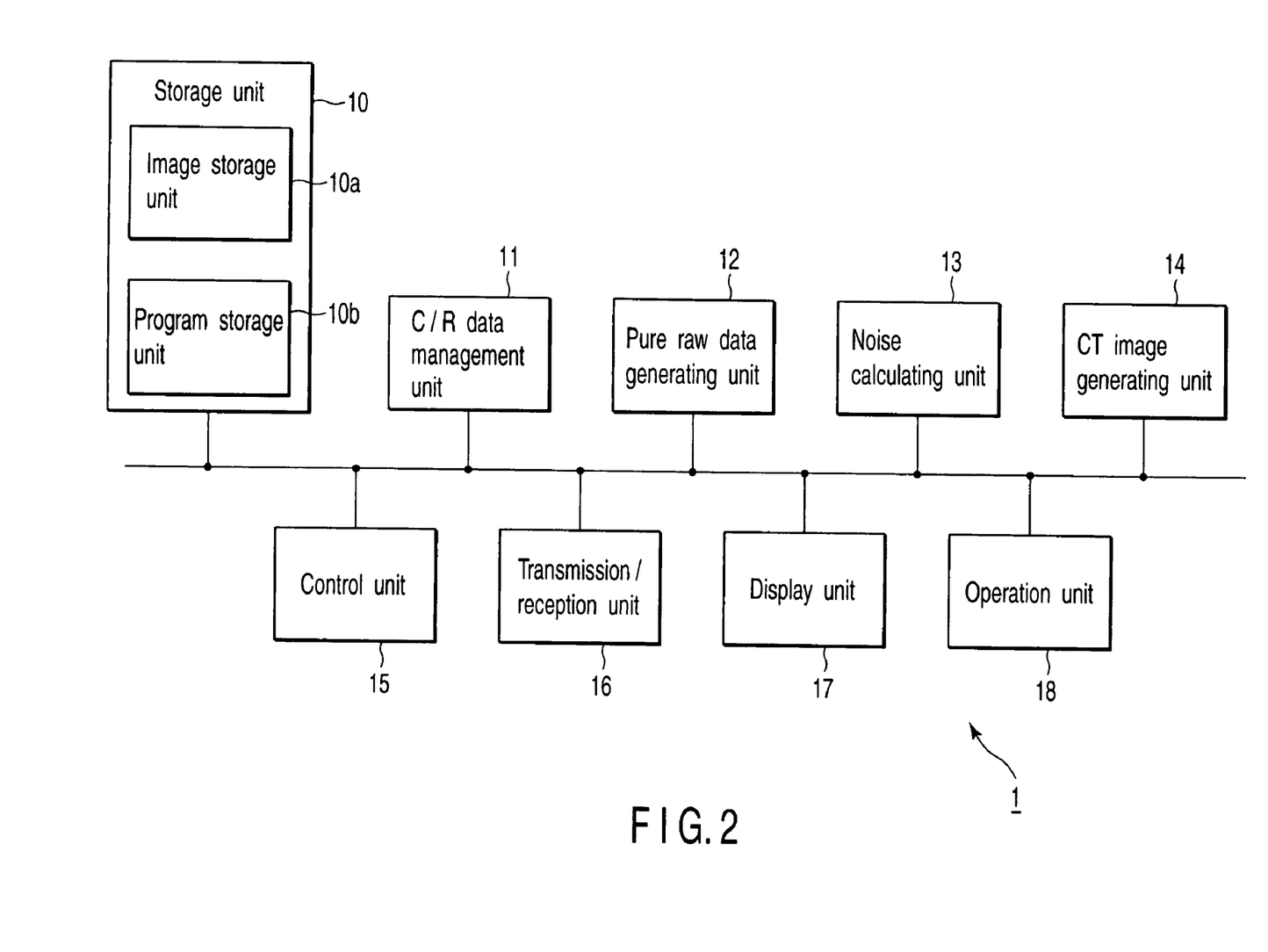
FIG. 2 is a block diagram showing the arrangement of the noise addition simulator 1 according to this embodiment.

FIG. 2 is a block diagram showing the arrangement of the noise addition simulator 1 according to this embodiment. As shown in FIG. 2, the noise addition simulator 1 comprises a storage unit 10, C/R data (calibration data/reference data) management unit 11, pure raw data generating unit 12, noise calculating unit 13, CT image generating unit 14, control unit 15, transmission/reception unit 16, display unit 17, and operation unit 18.

The storage unit 10 includes an image storage unit 10a and a program storage unit 10b. The storage unit 10 stores the raw data acquired by the X-ray computed tomography apparatus, CT images after reconstruction, and the like in correspondence with management information (for example, patient information (including physique information such as heights, weights, and the like), calibration data, reference data, and imaging conditions used to perform imaging for the images and the like). In this case, the calibration data is air calibration data (or water calibration data) acquired by applying X-rays to an air phantom (or water phantom), and is used to convert a photon count into a predetermined signal value. The reference data is data associated with the intensity of X-rays detected by a dedicated detector provided near an X-ray tube (i.e., exposed X-rays which are not transmitted through a subject) at the time of exposure of X-rays, and is used to normalize pure raw data (most initial data in X-ray CT operation which comprises the count of photons detected by each detection element of the imaging detector of the X-ray CT apparatus) when converting the pure draw data into raw data.

The program storage unit 10b stores a dedicated program for implementing the raw data server 31 and a program (noise addition simulation program) for implementing noise addition simulation (to be described later).

Note that the raw data server 31 loads the dedicated program in the program storage unit 10b into a memory (not shown) in the control unit 15, and is implemented by controlling the image storage unit 10a, the transmission/reception unit 16, and the like in accordance with the program.

The C/R data management unit 11 stores and manages information associated with correction processing executed when raw data is to be generated from pure raw data acquired in imaging operation of the X-ray computed tomography apparatus. More specifically, the C/R data management unit 11 stores a C/R data table which defines calibration data and reference data, which are used to generate pure raw data from raw data, for each X-ray computed tomography apparatus and each imaging condition.

The C/R data management unit 11 sends out, to the pure raw data generating unit 12, calibration data and reference data used for the generation of pure raw data when the pure raw data generating unit 12 generates pure raw data from raw data.

The pure raw data generating unit 12 generates pure raw data from raw data by performing inverse correction or the like using the calibration data and reference data received from the C/R data management unit 11.

The noise calculating unit 13 calculates a noise value on the basis of the number of photons applied for each detection element for the pure raw data generated by the pure raw data generating unit 12.

The CT image generating unit 14 generates a CT image by image reconstruction or the like using a noise value for each pixel which is calculated by the noise calculating unit 13.

The control unit 15 reads out programs stored in the program storage unit 10b, loads them into the memory, and statically or dynamically controls each unit or the overall system in accordance with the programs.

The transmission/reception unit 16 transmits/receives various kinds of data such as raw data and CT image data to/from other equipment such as an X-ray computed tomography apparatus through a network.

The display unit 17 displays a CT image (simulation image) on the basis of image data received from the CT image generating unit 14. The display unit 17 displays an I/F for noise addition simulation (to be described later) in a predetermined form.

The operation unit 18 comprises input devices such as a keyboard, a trackball, a mouse, and a dedicated interface for the execution of noise addition simulation (to be described above).

(Noise Addition Simulation Function)

The noise addition simulation function of the noise addition simulator 1 will be described next. This function is designed to generate pure raw data by using the raw data acquired from the raw data server 31 and execute noise addition simulation on the basis of the generated pure raw data.

Figure 3:
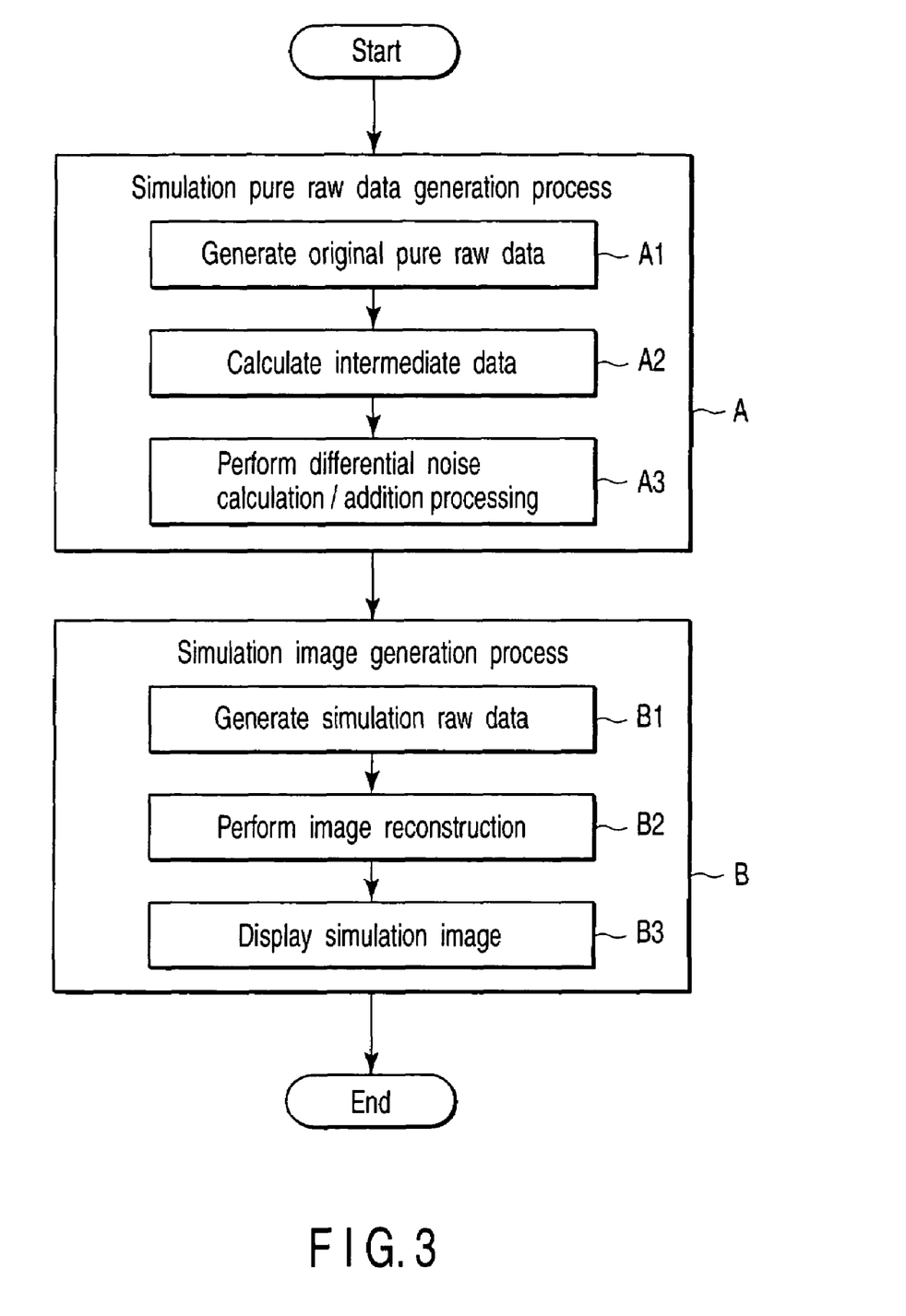
FIG. 3 is a flowchart showing the flow of simulation executed by a noise addition simulation function.

FIG. 3 is a view showing the flow of simulation executed by the noise addition simulation function. This simulation is roughly broken down into a simulation pure raw data generation process A and a simulation image generation process B using the simulation pure raw data. In the following description, raw data obtained by past imaging operation and stored in the image storage unit 10a will be referred to as "original raw data", and pure raw data for simulation which is generated on the basis of the original raw data will be referred to as "simulation pure raw data". It is also assumed that original raw data is acquired by an X-ray dose of 200 mAs, and a simulation image associated with an X-ray dose of 50 mAs is generated on the basis of the original raw data.

First of all, in the simulation pure raw data generation process A, original pure raw data is generated by adding calibration data and reference data to original raw data and performing inverse logarithmic transformation of the resultant data (step A1). The generated original pure raw data comprises a photon count for each detection element of the detector in the X-ray CT apparatus which has obtained raw data as a basis by imaging, and includes a noise component generated in the imaging operation.

It can be thought that as calibration data, data common to the X-ray CT apparatuses A to Z is used. If, however, different data are used for the respective apparatuses, the calibration data owned by the X-ray computed tomography apparatus which has obtained the raw data by imaging is used. In addition, as reference data, suitable data is selected on the basis of patient information input before the simulation.

Figure 4:
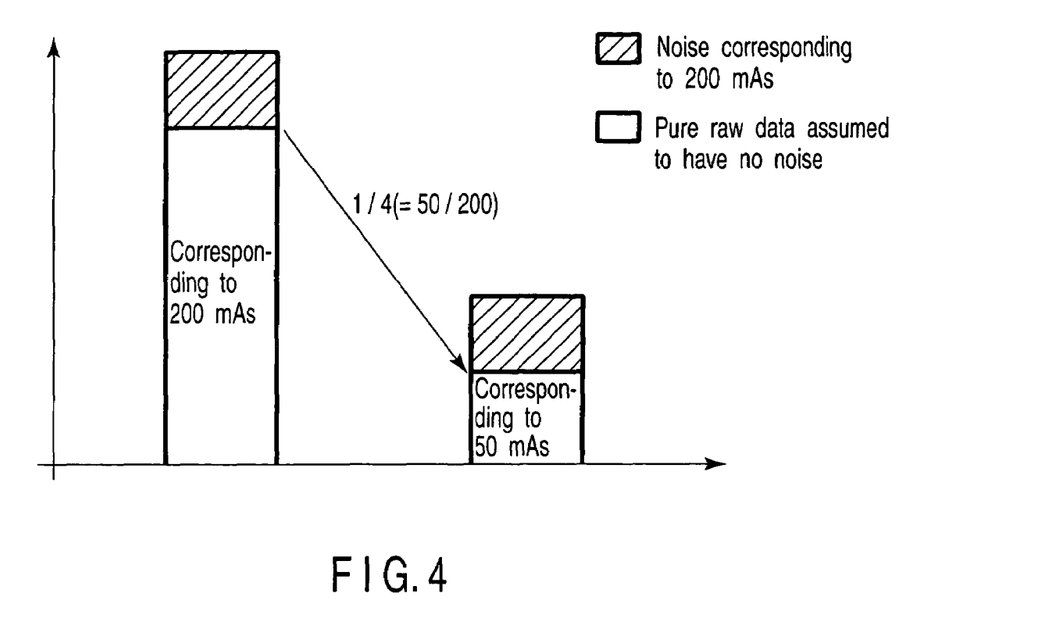
FIG. 4 is a graph showing a photon count (or a corresponding physical quantity) in a given detection element to explain intermediate data generation processing.

Intermediate data is generated next on the basis of the original pure raw data (step A2). As shown in FIG. 4, this intermediate data is generated by calculating a photon count L corresponding to an X-ray dose of 50 mAs from a quantitative value of the original pure raw data which contains no noise and adding noise corresponding to an X-ray dose of 200 mAs to the photon count.

Figure 5:
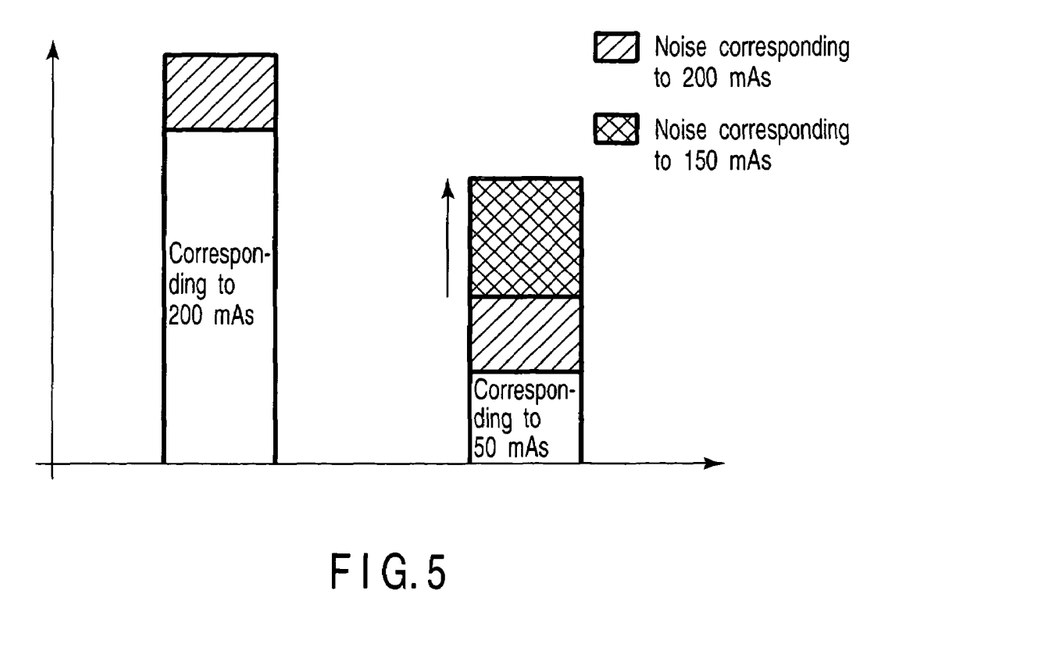
FIG. 5 is a graph conceptually showing simulation pure raw data obtained by adding noise to the intermediate data shown in FIG. 4.

As shown in FIG. 5, noise originating from the difference between a dose of 200 mAs and a dose of 50 mAs is calculated from, for example, Gaussian noise, and simulation pure raw data is generated by adding the noise to the photon count L (step A3). Note that although Gaussian noise is noise produced by using a Gaussian distribution, noise used for the simulation is not limited to Gaussian noise. Noise addition can be stopped at an arbitrary timing by pressing the "stop" button during the noise addition. In addition, the generated simulation pure raw data is preferably designed to allow addition of an arbitrary comment or the like which discriminates it from, for example, original raw data in consideration of data management.

Figure 6:
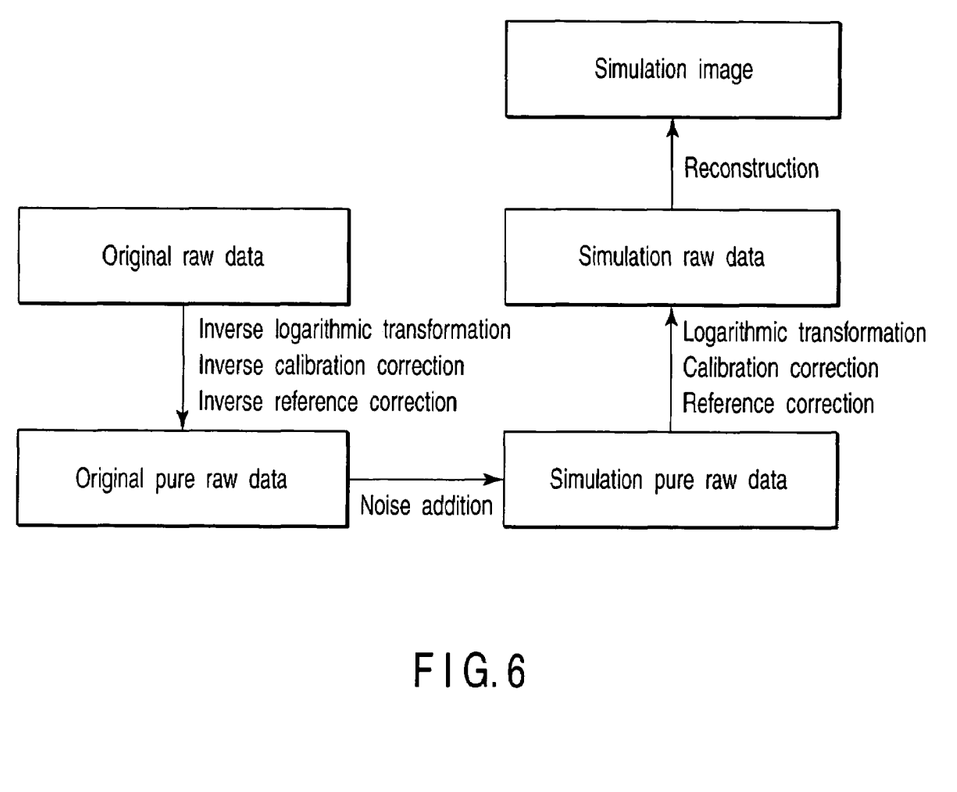
FIG. 6 is a view for explaining the relationship between original raw data, original pure raw data, simulation raw data, and simulation pure raw data.

The simulation image generation process B will be described next. First of all, as shown in FIG. 3, "simulation raw data" is generated by performing logarithmic transformation and correction using reference data and calibration data for the obtained simulation pure raw data (step B1). FIG. 6 shows the relationship between original raw data, original pure raw data, simulation raw data, and simulation pure raw data.

A simulation image is then generated and displayed by performing image reconstruction using the generated simulation raw data (steps B2 and B3).

Note that the image reconstruction executed in step B2 is executed on the basis of the input information using an image SD check window in advance.

Figure 7:
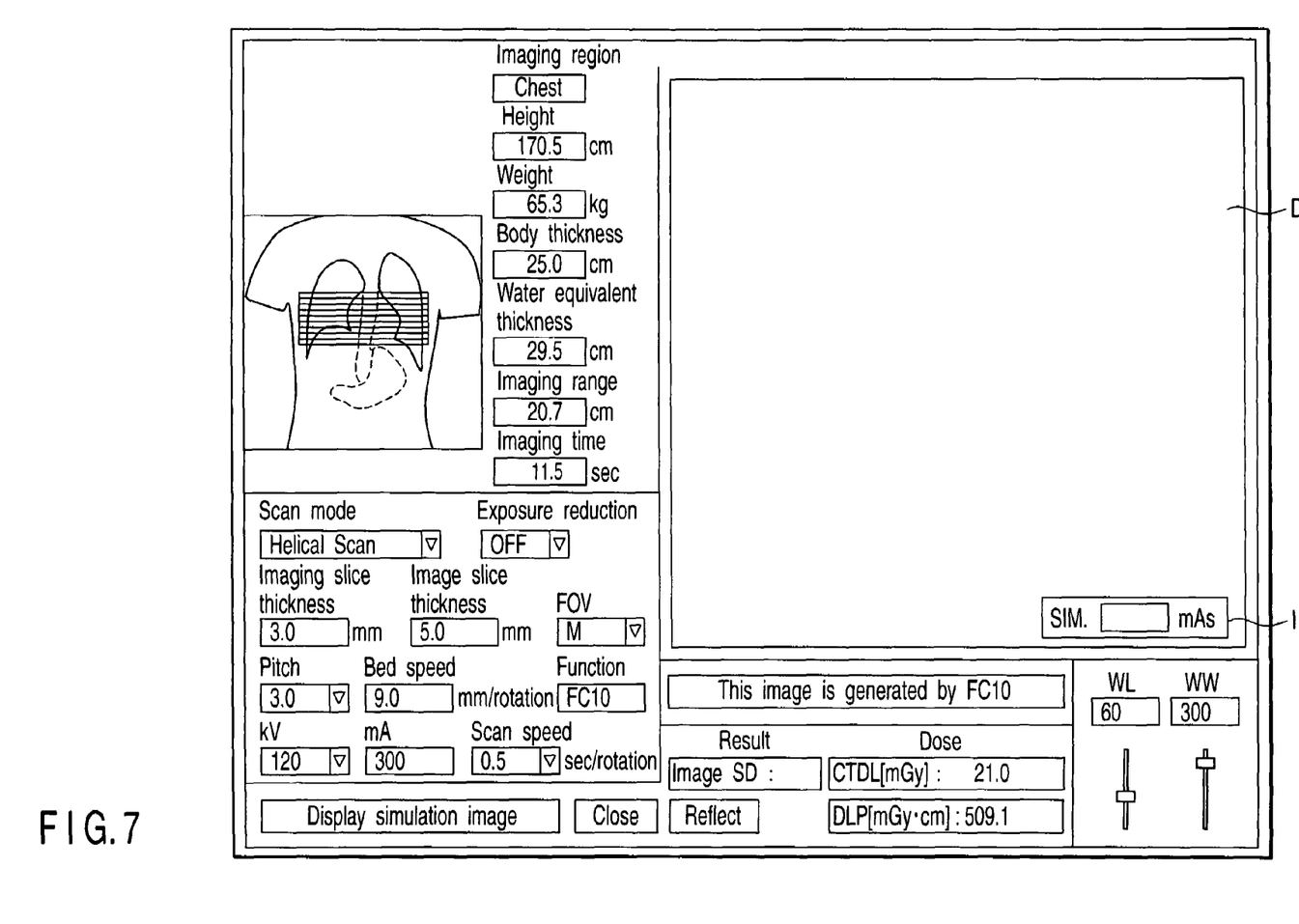
FIG. 7 is a view showing an example of an image SD check window.

FIG. 7 shows an example of an image SD check window. As shown in FIG. 7, the image SD check window includes a scanogram display area at the upper left portion, a simulation image display area at the upper right portion, an imaging region display box, a body thickness display box, a water equivalent thickness display box, an imaging range display box, an imaging time display box, a scan mode display box, an exposure reduction display box, an imaging slice thickness display box, an image slice thickness display box, an FOV display box, a beam pitch (Pitch) display box, a bed speed display box, a reconstruction function (function) display box, a tube voltage (kV) display box, a tube current (mA) display box, a scan speed display box, an image SD display box, a dose (CTDI, DLP) display box, and a window level/window width display box. In these display boxes, except for the body thickness display box, water equivalent thickness display box, and image SD display box, region names or numerical values of the corresponding items included in the scan plan data are initially entered.

A body thickness is numerically input on the image SD check window through the operation unit 18 or is calculated from scanogram data. A water equivalent thickness is calculated from the input or calculated body thickness according to a predetermined formula or is directly calculated from scanogram data. There are various methods of calculating a water equivalent thickness from a body thickness; an arbitrary method can be used. According to an example of a method of calculating a water equivalent thickness from a body thickness, the water equivalent thickness of the subject is estimated from the diameter of a water phantom on the basis of the ratio of a pixel value in a scanogram of the subject to the pixel value of the pre-acquired scanogram of a cylindrical water phantom having a known diameter. In practice, in order to reduce an error, the water equivalent thickness of the subject is estimated by multiplying the diameter of the water phantom by the square root of the ratio of the pixel value integral of a local area in a scanogram of the subject to the pixel value integral of a local area of the same size in a scanogram of a cylindrical water phantom having a known diameter.

The simulation image obtained by the above series of operations is the one generated by adding noise predicted with respect to most primitive pure raw data and using the resultant data. Therefore, this simulation result also reflects the influence of noise in correction such as calibration. In addition, since image reconstruction is performed on the basis of the conditions input through the window shown in FIG. 7, a simulation image which also includes the influence of image reconstruction processing can be acquired. As a consequence, accurate simulation also including noise produced in image reconstruction can be realized.

(Operation)

The operation of the noise addition simulator 1 will be described next.

Figure 8:
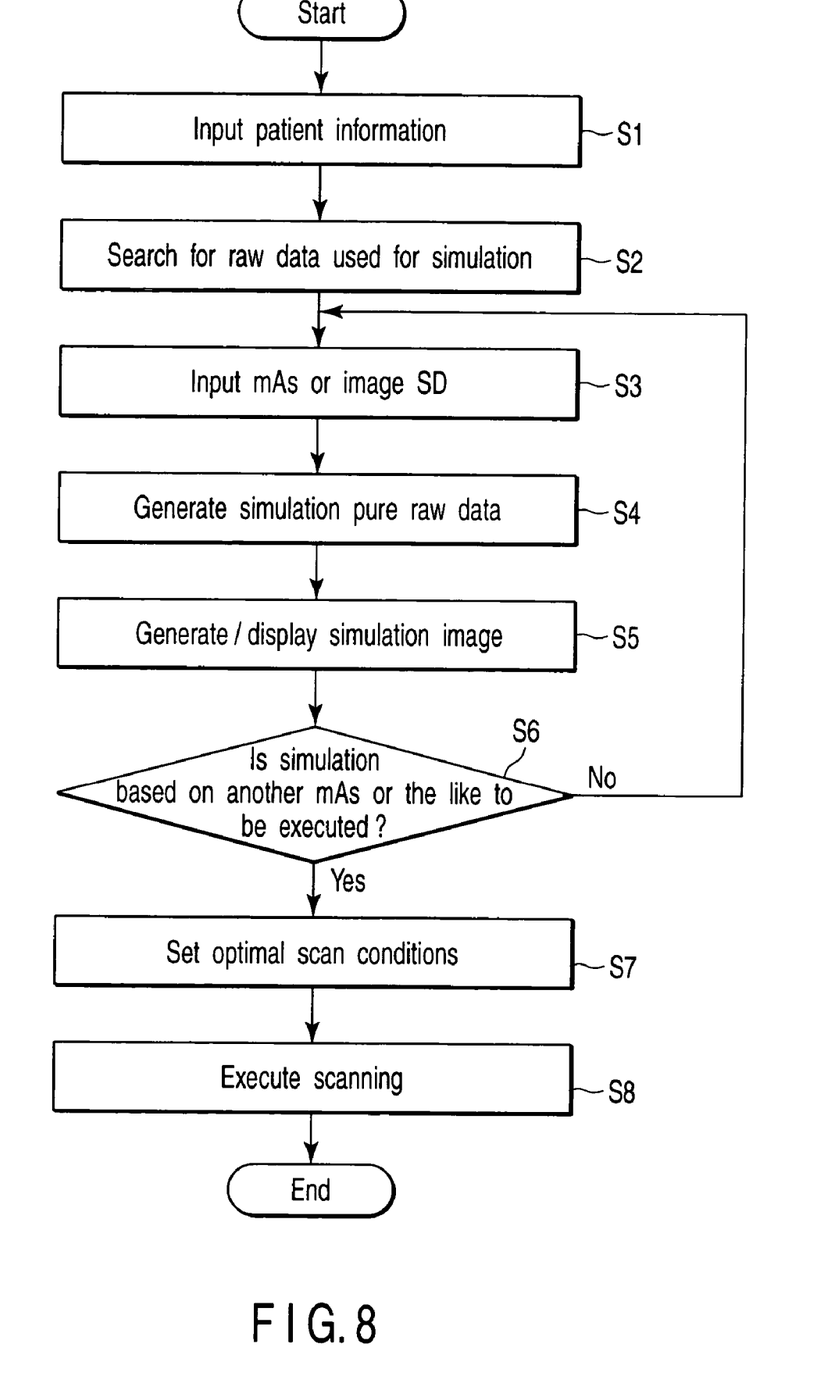
FIG. 8 is a flowchart showing the flow of processing from simulation processing by the noise addition simulator 1 to the execution of scanning by an X-ray computed tomography apparatus.

FIG. 8 is a flowchart showing the flow of processing from simulation processing by the noise addition simulator 1 to the execution of scanning by the X-ray computed tomography apparatus. First of all, patient information including patient physique information (a height, weight, body thickness, and the like) is input by using, for example, the window shown in FIG. 7 or the like (step S1). This input may be directly executed with the operation unit 18 or may be executed by transmission/reception to/from the RIS server through the network N.

The control unit 15 searches the raw data stored in the image storage unit 10a for the raw data of a patient who has a physique most similar to that of the patient of interest (step S2). Note that in step S1, the height, weight, and body thickness as physique information are all preferably input to allow a search for more suitable raw data. If, however, all the pieces of information cannot be obtained, a search in step S2 can be made by inputting at least one piece of information.

A dose of X-rays (mAs) used for simulation is then input (step S3). Note that the information to be input is not limited to a dose of X-rays (mAs), and an image SD may be input. Alternatively, a relative value (%) with respect to a dose of X-rays (mAs) in original raw data acquisition may be input.

The CT image generating unit 14 generates pure raw data for simulation from the input X-ray dose and the raw data obtained by the search. The display unit 17 displays the simulation image at, for example, a position D in the window shown in FIG. 7 (steps S4 and S5). The contents of the processing in these steps are the same as those described above. Note that when a simulation image is to be displayed, for example, as shown in FIG. 7, the image may be displayed together with information I indicating that the image is obtained by simulation. When the operator wants to display a simulation image on the X-ray computed tomography apparatus, the simulation image is automatically transmitted from the noise addition simulator 1 to the X-ray CT apparatus through the network N.

It is then determined whether to execute simulation based on another X-ray dose. If this simulation is to be executed, the processing in steps S3 to S5 is repeated. If it is not necessary to execute simulation based on another X-ray dose, optimal scan conditions are determined on the basis of the simulation result (step S7), and X-ray CT scanning is executed in accordance with the determined scan conditions (step S8).

According to the above arrangement, the following results can be obtained.

According to this noise addition simulation, noise addition simulation using simulation pure raw data is executed. Therefore, simulation can be realized with consideration also being given to noise produced in correction processing, image reconstruction, and the like when raw data is generated from pure raw data. In addition, since pure raw data is data before logarithmic transformation, it has a larger amount of information than general raw data. As a consequence, a simulation image similar to an image obtained by actual imaging operation as compared with the prior art can be generated. This allows even a doctor or technician with little experience to designate an X-ray dose based on reliable grounds and prevent unnecessary exposure of the subject.

According to this noise addition simulator, simulation pure raw data is generated by performing predetermined processing for original raw data. In general, the data size of pure raw data is much larger than that of raw data. For this reason, a large-capacity memory resource is required to manage pure raw data themselves. Therefore, this apparatus which essentially manages raw data to generate pure raw data can effectively use memory resources and improve practicability as compared with a case wherein pure raw data themselves are stored, and simulation images are generated by using them.

The present invention is not limited to the above embodiment, and can be embodied in the execution stage by modifying constituent elements within the spirit and scope of the invention. For example, the following are specific modifications.

Figure 9:
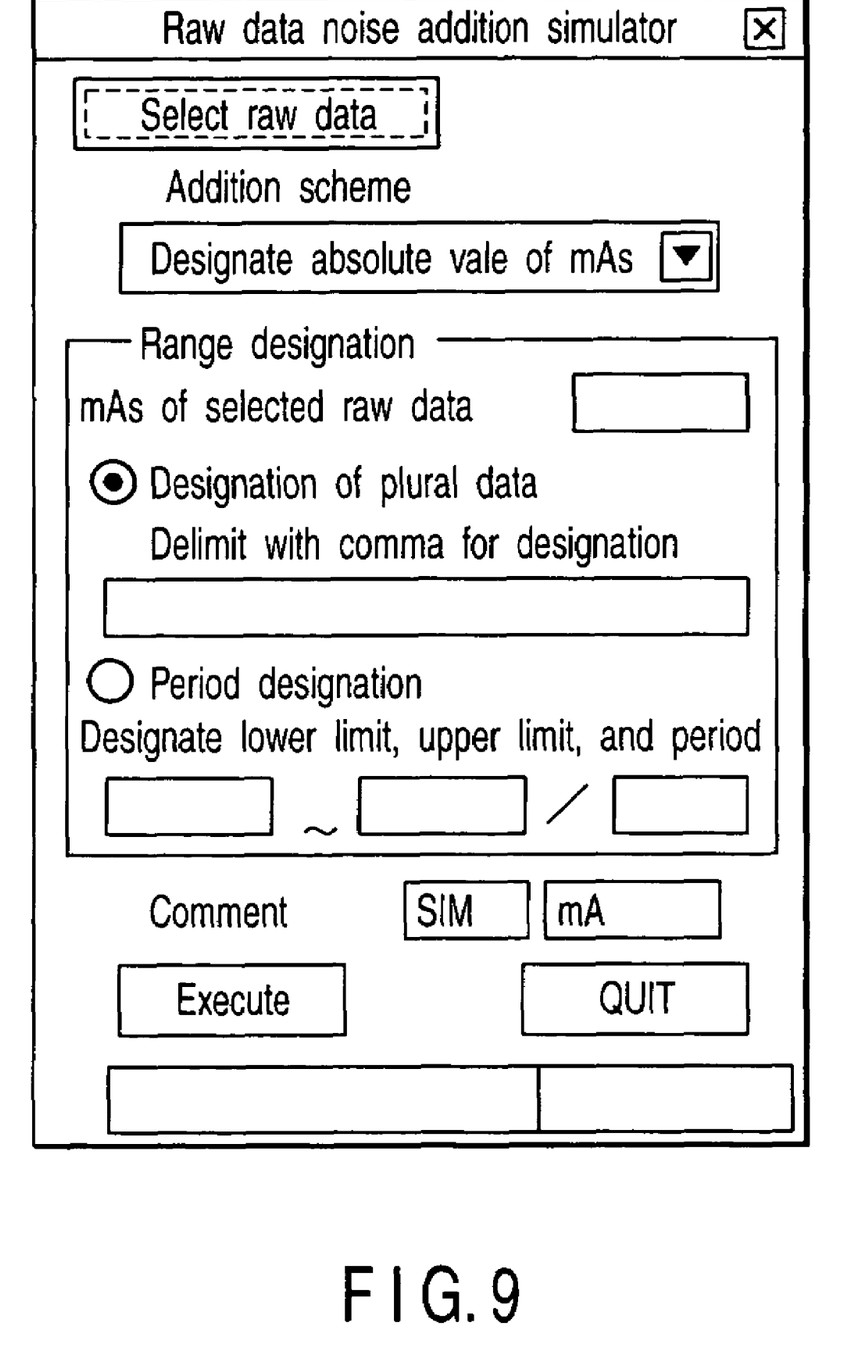
FIG. 9 is a flowchart for explaining the operation of the noise addition simulator 1.

(1) In the above embodiment, one value is input as an X-ray dose (mAs) used for simulation, and one simulation image corresponding to the input value is generated. In contrast to this, the present invention may be configured to allow a plurality of X-ray doses (mAs) to be input and concurrently generate simulation images corresponding to the respective values. As an input technique for this arrangement, for example, there is available a technique of randomly inputting arbitrary values or a technique of setting the upper limit, lower limit, and period of X-ray doses (mAs) and automatically inputting X-ray doses (mAs) in the range determined by the upper and lower limits in accordance with the period. FIG. 9 shows an example of an input interface based on the latter technique. According to such an arrangement, inputting of a plurality of X-ray doses (mAs) can be simplified, and simulation images based on different X-ray doses (mAs) can be simultaneously observed and compared.

(2) The above embodiment has exemplified the case wherein raw data before calibration and logarithmic transformation is stored in advance, and simulation is executed on the basis of the stored data. However, the present invention is not limited to this. For example, raw data after calibration and logarithmic transformation may be stored, and simulation may be executed upon adding noise calculated by a predetermined technique to the raw data.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. A medical image display apparatus which generates a computed tomogram, which is to be obtained by X-ray computed tomography, by simulation in a simulated manner, comprising:

a storage unit which stores first projection data which is raw data obtained on the basis of exposure of X-rays to a subject to be examined;

an input unit to input information with respect to X-ray dose;

a calculation unit which calculates noise information on the basis of the information with respect to X-ray dose;

a projection data generating unit which generates second projection data on the basis of the first projection data and the noise information, the second projection data being obtained by performing predetermined processing at least including inverse logarithmic transformation for the raw data and being predicted to be obtained by X-ray computed tomography using the information with respect to X-ray dose; and an image generating unit which generates a simulation image by using the second projection data;

wherein the predetermined processing further includes first addition processing of adding calibration processing to the raw data and second addition processing of adding reference information to the raw data, the reference information being associated with the intensity of X-rays detected by a dedicated detector provided near an X-ray tube to detect exposed X-rays which are not transmitted through a subject at the time of exposure of X-rays.

2. An apparatus according to claim 1, wherein the information with respect to X-ray dose is an X-ray dose used for the simulation.

3. An apparatus according to claim 2, wherein the noise information is information associated with noise originating from a difference between the X-ray dose used to acquire the first projection data and the X-ray dose used for the simulation.

4. An apparatus according to claim 1, wherein the projection data generating unit generates information associated with a photon count and noise, which are predicted to be detected by a plurality of X-ray detection elements in X-ray computed tomography using the X-ray dose for the simulation, on the basis of the first projection data and the noise information, and generates the second projection data on the basis of the information associated with the photon count and the noise.

5. An apparatus according to claim 2, wherein when a plurality of X-ray doses used for the simulation are input by the input unit, the calculation unit calculates a plurality of pieces of noise information corresponding to the respective X-ray doses used for the simulation, and the projection data generating unit generates a plurality of second projection data, which are predicted to be obtained by X-ray computed tomography using said respective input X-ray doses, on the basis of the first projection data and said respective pieces of noise information, and generates a plurality of simulation images corresponding to said plurality of X-ray doses used for the simulation by using said plurality of second projection data.

6. An apparatus according to claim 5, wherein the input unit includes an interface to input a plurality of X-ray doses used for the simulation used for the simulation by setting an upper limit value, a lower limit value, and a period.

7. An apparatus according to claim 1, further comprising a display unit which displays the simulation image together with information indicating that the image is obtained by simulation.

8. An apparatus according to claim 1, which further comprises a selection unit which selects the first projection data used for the simulation on the basis of input physique information of the subject when the storage unit stores the first projection data associated with a plurality of subjects, and in which the projection data generating unit generates the second projection data by using the selected first projection data.

9. An X-ray computed tomography apparatus comprising:

a storage unit which stores first projection data which is raw data obtained on the basis of exposure of X-rays to a subject to be examined;

an input unit to input information with respect to X-ray dose used for the simulation;

a calculation unit which calculates noise information on the basis of the information with respect to X-ray dose;

a projection data generating unit which generates second projection data on the basis of the first projection data and the noise information, the second projection data being obtained by performing predetermined processing at least including inverse logarithmic transformation for the raw data and being predicted to be obtained by X-ray computed tomography using the information with respect to X-ray dose, and an image generating unit which generates a simulation image by using the second projection data;

wherein the predetermined processing further includes first addition processing of adding calibration processing to the raw data and second addition processing of adding reference information to the raw data, the reference information being associated with the intensity of X-rays detected by a dedicated detector provided near an X-ray tube to detect exposed X-rays which are not transmitted through a subject at the time of exposure of X-rays.

* * * * *